US006814986B1

(12) United States Patent
Rombi

(10) Patent No.: US 6,814,986 B1
(45) Date of Patent: Nov. 9, 2004

(54) COMPOSITION FOR TREATING OBESITY AND ESTHETIC TREATMENT PROCESS

(75) Inventor: Max Rombi, Bordighera (IT)

(73) Assignee: Laboratoires Arkopharma, Carros (FR)

( * ) Notice: Subject to any disclaimer, the term of this patent is extended or adjusted under 35 U.S.C. 154(b) by 0 days.

(21) Appl. No.: 09/601,019

(22) PCT Filed: Jan. 14, 2000

(86) PCT No.: PCT/FR00/00065

§ 371 (c)(1),
(2), (4) Date: Oct. 17, 2000

(87) PCT Pub. No.: WO00/41708

PCT Pub. Date: Jul. 20, 2000

(30) Foreign Application Priority Data

Jan. 14, 1999 (FR) .............................. 99 00328

(51) Int. Cl.$^7$ ............................................... A61K 35/78
(52) U.S. Cl. ....................... 424/749; 424/725; 424/774; 424/779
(58) Field of Search ...................... 424/195.1; 252/398, 252/404; 560/69, 399

(56) References Cited

U.S. PATENT DOCUMENTS 4,673,530 A * 6/1987 Hara ........................... 252/398
5,776,756 A * 7/1998 Kimura et al. ............... 435/189

FOREIGN PATENT DOCUMENTS

| EP | 0456 023 A1 | 11/1991 |
| JP | 60114153 | * 6/1985 |
| JP | 60/114158 | 6/1985 |

OTHER PUBLICATIONS

Fetro et al. Green Tea; The Complete Guide to Herbal Medicines (Sep. 2000), Simon & Schuster, Inc, New York, NY, p. 253.*

Chantre et al. Recent Findings of Green Tea Extract AR25 (Exolise) and its Activity for the Treatmen of Obesity; Phytomedicine 9: 3–8, 2002.*

Dulloo et al. Efficacy of a Green Tea Extract Rich in Catechin Polyphenols and Caffeine in Increasing 24–H Energy Expenditure and Fat Oxidation in Humans; Am. J. Clin. Nutr. (Dec. 12, 1999) 70: 1040–1045.*

Forman, J. Still No Quick Fix for Obesity Still No Quick Fix for Obesity; Boston Globe, Article, (Oct. 22, 2002) p 1–2.*

Gruenwald et al. ed. *Camellia Sinensis*; PDR for Herbals (1998) Medical Economics Company Inc., Montvale, NJ, p. 710.*

Yasuda et al., Nippon Shokuhin Kogyo Gakkaishi, "Inhibitory Effect of Tea Catechins on Halitosis and Their Application to Chewing Gum", *Journal of the Japanese Society of Food Industry*, vol. 38, No. 12, 1098–1102 (1991).

Kakuda, T., et al., "Effects of Tea (*Camellia sinensis*) Chemical Compounds on Ethanol Metabolism in ICR Mice", Biosci. Biotech. Biochem., 60(9), 1450–1454, 1996.

Yen, Gow–Chin, "Relationship Between Antimutagenic Activity and Major Components of Various Teas", Mutagenesis, vol. 11, No. 1, pp. 37–41, 1996, Oxford University Press.

Dulloo, A.G., et al., "Tealine and Thermogenesis: Interactions Between Polyphenols, Caffeine and Sympathetic Activity", p. 71, 08–178–WA1, 1996 University of Geneva, Switzerland.

Chemical Abstracts, RN 154–23–4 Oct. 12, 2002.
Chemical Abstracts, RN 989–51–5 Oct. 12, 2002.
Akio, *Patent Abstracts of Japan*, vol. 009, No. 260 (Oct. 17, 1985). Abs Only.
Paschka et al., *Cancer Letters*, 130(1–2):1–7 (1998).

* cited by examiner

*Primary Examiner*—Patricia Leith
(74) *Attorney, Agent, or Firm*—Burns, Doane, Swecker & Mathis, L.L.P.

(57) ABSTRACT

The invention relates to a composition for the curative and prophylactic treatment of obesity, comprising a catechol-rich extract of green tea, in particular containing from 20% to 50% by mass of catechols expressed as epigallocatechol gallate (EGCG).

8 Claims, No Drawings

COMPOSITION FOR TREATING OBESITY AND ESTHETIC TREATMENT PROCESS

The present invention relates to the general field of treating obesity. The invention is directed in particular toward compositions for the curative and prophylactic treatment of obesity, but it also relates to the esthetic treatment of a human being to enhance his or her figure.

The therapeutic objective as regards obesity is well defined: it is a matter either of allowing the individual to lose a significant amount of weight, or of helping the individual to maintain a weight level which is as low as desired.

Several types of approach have been envisaged to date.

Nutritional approaches are directed toward reducing the supply of energy in the form of foods. This can be achieved either by drastically reducing the energy supplies or by replacing high-energy nutrients with others which are lower in energy: such as indigestible substitute fats, structured triglycerides which are difficult to assimilate or dietary fibers which cannot be assimilated.

The therapeutic approaches may have a variety of targets. Reducing the food intake may be the first objective. Attempts to reduce the food intake may be made by using anorexigenic substances, whose short-term effects are proven, but whose duration of use is limited on account of adverse side effects. In fact, very few of these products can truly be used and their long-term efficacy remains highly debated. New molecules are undergoing assessment or may do so in the near future, but their value still remains to be shown.

A second objective may be to increase the expenditure of energy by using thermogenic substances which act at the central or peripheral level. The use of these substances still remains limited.

A third objective is to reduce the assimilation of the dietary lipids, or optionally even that of the carbohydrates. This is a more recent approach, but is gaining in interest. A reduction in the assimilation of the dietary lipids may be obtained either by reducing the activity of the digestive enzymes concerned, or by modifying the properties of the interfaces transporting the lipid molecules, emulsions, vesicles or micelles.

The traditional use of tea is in the form of an infusion, for which the tip of the stems, comprising the last two leaves and the bud, are used. After harvesting, these leaves may be subjected to a fermentation, resulting in a transformation of the chemical substances they contain and in particular the catechols, which corresponds to black tea, or else may be dried immediately, thus giving green tea.

Besides catechols, tea contains caffeine, the diuretic effect of which is well known. This diuretic effect is the reason for the traditional use of green tea as a medicinal plant to promote the elimination of water by the kidneys, either in the case of urinary disorders or as a supplement to weight-reducing diets. The presence of caffeine is also the reason for the traditional use of tea in conditions of fatigue (asthenia).

Numerous epidemiological studies carried out on certain populations have clearly demonstrated the beneficial effects of the chronic ingestion of tea, and more particularly of green tea. Thus, the long-term consumption of green tea is thought to be anti-atherogenic on account of its hypocholesterolemiant effects (Muramatsu et al. 1986, Yang et al. 1997) and its ability to prevent the oxidation of LDLs in the circulation (Tijburg et al. 1997). Green tea is also known for its anti-mutagenic and anti-carcinogenic effects. Thus, it has been shown that green tea significantly reduces the risk of colorectal, skin and breast cancers (Blot et al. 1997, Conney et al. 1997, Dreosti et al. 1997, Jankun et al. 1997, Ji et al. 1997).

The traditional use of green tea as a diuretic is currently performed in the form of infusions, liquid extracts, extracts of plant powders or extracts in gel capsules or tablets. In these various forms, the green tea, often combined with another diuretic plant, is generally used at a dose corresponding to 1 to 3 g of plant per day.

In the context of screening pharmacological properties of various plants, it has been discovered that extracts of green tea have noteworthy properties which allow them to be used in the treatment of obesity.

The human body continually expends energy in order to function. The origins of this expenditure of energy are threefold: the metabolism, muscular work and thermogenesis, which corresponds to the energy expended by the body to maintain a constant temperature.

The expenditure of energy is compensated for by the energy supplied by the assimilation of foods. If the energy supplied from the dietary ration is strictly identical to the energy expended, the individual maintains a stable weight. If there is an excess supply of energy, the body stores this energy in the form of fats (increase in weight), and if there is a deficit in the supply of energy, the body draws the energy it lacks by burning off the fats stored (loss of weight). However, in this latter situation of an energy deficit encountered in the course of weight-reducing diets, the body reacts to save energy and reduce thermogenesis. This is the control mechanism which accounts for the failure of weigh-reducing diets. Specifically, after losing weight for a few weeks, the individual's weight stabilizes. If they wish to continue to slim, they must further reduce their food intake.

The full value of being able continually to increase thermogenesis, in particular in the course of a low-calorie diet during which it is lowered, may thus be appreciated. Various chemical substances stimulate thermogenesis, such as nicotine, ephedrine, aspirin, caffeine, etc., but none of them has made it possible to produce a medicinal product for treating obesity since the doses required to obtain an increase in thermogenesis entail considerable side effects, which are incompatible with a treatment which is necessarily long-lasting, generally extending over several months.

This objective has been achieved in accordance with the present invention by means of a composition for the curative and prophylactic treatment of obesity, comprising an extract of green tea, Camellia sinensis, which is rich in catechols.

The present invention is also directed toward the use of an extract or powder of green tea which has anti-lipase and/or thermogenic properties, for the manufacture of a medicinal product intended for the curative and prophylactic treatment of obesity.

Finally, the present invention relates to a process for the esthetic treatment of a human being in order to enhance his or her figure, characterized in that it involves the oral administration of a catechol-enriched extract of green tea in order to bring about a loss of weight or to maintain a weight level which is as low as desired.

In the context of the present invention, the extract of green tea contains from 20% to 50%, in particular from 20% to 30%, by mass of catechols expressed as epigallocatechol gallate (EGCG).

The content of catechols, expressed as epigallocatechol gallate (EGCG), is, for example, advantageously determined in the context of the present invention by using the analytical method described below.

The process is performed by liquid chromatography.

Solution to be examined: 80 ml of methanol R are added to 0.200 g of extract. The mixture is placed under magnetic stirring for 5 min and then in an ultrasound bath for 5 min.

The resulting mixture is filtered through paper and the volume is made up to 100 ml with the same solvent. This solution is diluted fivefold with methanol R.

Caffeine stock solution: 30 mg of caffeine are dissolved in methanol and made up to 100 ml with the same solvent.

Epigallocatechol gallate stock solution: 6 mg of epigallocatechol gallate (EGCG) are dissolved in methanol and made up to 10 ml with the same solvent.

Control solution: 1 ml of each stock solution is taken and made up to 10 ml with the same solvent.

The chromatography can be carried out using:
- a stainless steel column of length 250 mm and inside diameter 4.6 mm, filled with octadecylsilyl silica gel for chromatography R (5 μm) and thermostatically maintained at 200° C. (Nucleosil C18) and a precolumn having the same characteristics as the column,
- as mobile phase, at a flow rate of 1 ml/min, a mixture of aqueous 2% V/V glacial acetic acid solution (A) and of acetonitrile (B), the linear elution gradient of which is as follows:

| Time (min) | A (%) | B (%) |
|---|---|---|
| 0 | 95 | 5 |
| 5 | 95 | 5 |
| 10 | 90 | 10 |
| 17 | 85 | 15 |
| 30 | 82 | 18 |
| 35 | 82 | 18 |
| 40 | 95 | 5 | as detector, a spectrophotometer set at 278 nm.

10 μl of each of the solutions are injected separately, at least twice. The sensitivity of the detector is adjusted so as to obtain peaks whose height represents at least 50% of the total scale of the recorder.

The percentage caffeine content is calculated using the following expression:

$$\frac{SCE}{SCT} \times \frac{MCT}{MCE} \times 0.05$$

SCE: area of the peak corresponding to caffeine in the chromatogram obtained with the solution to be examined
SCT: area of the peak corresponding to caffeine in the chromatogram obtained with the control solution
MCE: test sample of extract in the solution to be examined, expressed in grams
MCT: test sample of caffeine in the control solution, expressed in milligrams.

The percentage content of catechols expressed as epigallocatechol gallate (EGCG) is calculated using the following expression:

$$\frac{\Sigma SE}{ST} \times \frac{MT}{ME} \times 0.5$$

ΣSE: sum of the areas of the peaks (2-5-6-7-8) corresponding to catechols in the chromatogram obtained with the solution to be examined
ST: area of the peak corresponding to the EGCG in the chromatogram obtained with the control solution
ME: test sample of extract in the solution to be examined, expressed in grams
MT: test sample of EGCG in the control solution, expressed in milligrams.

It should be pointed out that the epigallocatechol gallate represents on average about 70% of all the catechols present in an extract of green tea, with a range of between 50% and 90%.

According to one particular characteristic of the present invention, the extract of green tea contains from 5% to 10% by mass of caffeine.

According to another characteristic of the invention, the extract of green tea has a ratio of the concentration of catechols to the concentration of caffeine of between 2 and 10.

According to one preferred characteristic of the invention, the extract of green tea is titrated so as to allow the administration of a daily dose of from 250 mg to 500 mg, preferably about 375 mg, of catechols per day, and from 50 mg to 200 mg, preferably about 150 mg, of caffeine per day.

The increase in thermogenesis in rats by an extract of green tea according to the invention was studied according to the following protocol:

The oxygen consumption of rats, maintained in a hermetic chamber for two hours and more, is measured after administering the test product. Since the expenditure of energy is proportional to the oxygen consumption, this technique makes it possible to measure the increase in thermogenesis, the basal metabolism and the muscular work being constant before and after treatment.

The test product was an extract of green tea containing 24.7% catechols and 8.35% caffeine.

The following results were obtained:
Controls: 0.06 w/kg$^{0.75}$
0.5 mg of extract/kg: 0.45 w/kg$^{0.75}$
1.0 mg of extract/kg: 0.81 w/kg$^{0.75}$
2.0 mg of extract/kg: 1.10 w/kg$^{0.75}$ The increase in thermogenesis in man by an extract of green tea according to the invention was also determined.

A similar study was carried out on 10 volunteers receiving at each meal either 500 mg of an extract of green tea (corresponding to 125 mg of catechols and 50 mg of caffeine), or 50 mg of caffeine, or a placebo.

The total expenditure of energy over 24 h showed a statistically significant increase ($p<0.01$) in favor of the extract: 9867 kJ compared with 9538 kJ for the placebo and 9599 kJ for caffeine.

These results demonstrate the ability of an extract of green tea according to the invention to significantly increase thermogenesis. This property is not associated with the caffeine content of the extract, since the administration of caffeine alone, at the same dose as that provided by the extract of green tea, does not increase thermogenesis.

Furthermore, the fact that the significant decrease in the Respiratory Quotient is not accompanied by an increase in the urinary excretion of nitrogen, makes it possible to conclude that there has been an increase in the oxidation of lipids, which is the desired aim in any treatment of obesity.

Finally, it has been possible to demonstrate that the extract of green tea according to the invention leads to an inhibition of the digestive lipases. An in vitro study made it possible to demonstrate that the extract of green tea, at a dose of 6 mg of extract per 100 mg of lipids, partially eliminates the emulsification of the lipids, both in the stomach and in the intestine. As it is known that the emulsification of lipids is the essential step in the action of lipases on food lipids, these results may account for the inhibitory ability of digestive lipases.

Another in vitro study, carried out under conditions reproducing the physiological conditions (successive action on triolein of gastric lipase and then of pancreatic lipase)

demonstrated that the extract of green tea, at a dose of 6 mg/100 mg of lipids, allows virtually total inhibition of the gastric lipase (89% inhibition) and partial inhibition of the pancreatic lipase (32% inhibition), i.e. a total inhibition of lipolysis of close to 40%.

The use of a powder of green tea which has an intrinsically lower dose of catechols and/or caffeine, but in a larger amount making it possible to manufacture a medicinal product which has anti-lipase and/or thermogenic properties, obviously also falls within the context of the present invention.

In the context of the present invention, in vitro studies were carried out to demonstrate the existence of synergy between epigallocatechol gallate and caffeine. These studies were carried out on an ex vivo pharmacological model of thermogenesis. The principle is to measure the oxygen consumption of a sample of rat brown adipose tissue; the oxygen consumption is proportional to the thermogenesis induced in the adipose tissue by the various test substances.

The results below indicate the increase in oxygen consumption as a function of the concentration of EGCG and/or of caffeine.

| Caffeine | 100 µM | 0 | 0 | 100 µM | 100 µM |
|---|---|---|---|---|---|
| EGCG | 0 | 100 µM | 200 µM | 100 µM | 200 µM |
| Increase in oxygen consumption | no effect | no effect | +40% | no effect | +140% |

These results clearly demonstrate the existence of synergistic stimulation of thermogenesis for a concentration of 200 µM of EGCG and 100 µM of caffeine, i.e. an EGCG/caffeine ratio of 2.

Given the other pharmacological effects of caffeine (tachycardia, insomnia), it may thus be desirable, in order to increase thermogenesis, to limit the amount of caffeine and to increase the EGCG/caffeine ratio. For this reason, according to one advantageous variant of the invention, this ratio will preferably be between 2 and 10.

EXAMPLE OF OBTAINING AN EXTRACT OF GREEN TEA

Green tea contains on average 6% to 7% catechols and 2% to 3% caffeine.

In order to obtain the properties of increasing thermogenesis and of inhibiting digestive lipases which are described above, a sufficient supply of catechols is necessary. It is thus necessary to carry out an extraction of the green tea making it possible to obtain an extract which is sufficiently concentrated in catechols.

By way of example, the following extraction process can be used: 1 kg of the tips of ground stems, comprising the last two leaves and the bud, of green tea are extracted by percolation for 6 to 8 h with 10 kg of 80% ethanol (m/m). After filtration, the extract is concentrated under partial vacuum at a maximum temperature of 60° C. The concentrated extract is then spray-dried at a maximum temperature of 250° C. with or without maltodextrin, depending on the plotter specifications selected. This process gives an extract containing 20% to 30% catechols and 5% to 10% caffeine This example is not limiting, and other extraction processes for obtaining an extract which is sufficiently rich in catechols can be used, in particular by varying the proportions of water and ethanol, or by using other solvents such as water, ethyl acetate, methanol, etc., alone or in combination. The choice of solvents selected will make it possible to vary the catechol and caffeine contents, the objective being a high catechol content, since the catechols are the main source of the pharmacological properties demonstrated above.

In this context, the use of green tea which has been partially decaffeinated beforehand by any extraction process which does not have a negative effect on the catechols (for example methylene chloride or supercritical carbon dioxide) may be entirely envisaged in order to obtain a tea extract containing only a small percentage of caffeine.

Without at all wishing to be limited to such an interpretation, it appears likely that the mechanism of activity of the extracts of green tea, which is the subject of the present invention, can be explained as follows. The catechols present in high concentration in the extracts of green tea according to the invention exert an inhibitory effect on catechol-O-methyltransferase (COMT), whereas the caffeine concentration of the extracts of green tea according to the invention acts by inhibiting phosphodiesterases, which leads to a reinforced activity of noradrenalin on thermogenesis.

What is claimed is:

1. A composition for the treatment of obesity, suitable for oral administration, comprising an extract of green tea having from 20% to 50% by mass of catechols expressed as epigallocatechol gallate (EGCG), and from 5% to 10% by mass of caffeine, the ratio of the concentration of catechols to the concentration of caffeine in said extract being between 2 and 10.

2. A composition according to claim 1, wherein said green tea extract has from 20% to 30% by mass of catechols expressed as epigallocatechol gallate (EGCG).

3. The composition according to claim 1, wherein said green tea extract has from 250 mg to 500 mg of catechols, and from 50 mg to 200 mg of caffeine, per daily dose.

4. The composition according to claim 3, wherein said green tea extract has about 375 mg of catechols and about 150 mg of caffeine.

5. A composition for the treatment of obesity, suitable for oral administration, comprising an extract of green tea having from 20% to 50% by mass of catechols expressed as epigallocatechol gallate (EGCG), and from 5% to 10% by mass of caffeine, the ratio of the concentration of catechols to the concentration of caffeine in said extract being between 2 and 10 and wherein said green tea extract is obtained using an 80% ethanol extraction.

6. The composition according to claim 5, wherein said green tea extract has from 20% to 30% by mass of catechols expressed as epigallocatechol gallate (EGCG).

7. The composition according to claim 5, wherein said green tea extract has from 250 mg to 500 mg of catechols, and from 50 mg to 200 mg of caffeine, per daily dose.

8. The composition according to claim 7, wherein said green tea extract has about 375 mg of catechols and about 150 mg of caffeine.

* * * * *